US011490899B2

United States Patent
Beverland et al.

(10) Patent No.: US 11,490,899 B2
(45) Date of Patent: Nov. 8, 2022

(54) SURGICAL DEVICE AND METHOD

(71) Applicant: DEPUY IRELAND UNLIMITED COMPANY, Ringaskiddy (IE)

(72) Inventors: David Beverland, Leeds (GB); Conor Lowry, Leeds (GB); Mark Tomlinson, Leeds (GB); Duncan Young, Leeds (GB)

(73) Assignee: DEPUY IRELAND UNLIMITED COMPANY

( * ) Notice: Subject to any disclaimer, the term of this patent is extended or adjusted under 35 U.S.C. 154(b) by 48 days.

(21) Appl. No.: 16/973,189

(22) PCT Filed: Apr. 29, 2019

(86) PCT No.: PCT/EP2019/060976
§ 371 (c)(1),
(2) Date: Dec. 8, 2020

(87) PCT Pub. No.: WO2020/001832
PCT Pub. Date: Jan. 2, 2020

(65) Prior Publication Data
US 2021/0259705 A1 Aug. 26, 2021

(30) Foreign Application Priority Data

Jun. 26, 2018 (GB) ...................................... 1810477
Mar. 27, 2019 (GB) ...................................... 1904256

(51) Int. Cl.
*A61B 17/17* (2006.01)
*A61B 17/15* (2006.01)
*A61B 90/00* (2016.01)
(52) U.S. Cl.
CPC .............. *A61B 17/15* (2013.01); *A61B 90/06* (2016.02); *A61B 2090/061* (2016.02)

(58) Field of Classification Search
CPC ................ A61B 17/742; A61B 17/175; A61B 2090/061; A61B 90/06
See application file for complete search history.

(56) References Cited

U.S. PATENT DOCUMENTS 4,621,630 A 11/1986 Kenna
4,959,066 A 9/1990 Dunn et al.
(Continued)

FOREIGN PATENT DOCUMENTS

AU 2006200152 A1 8/2006
EP 1797834 A1 6/2007
(Continued)

OTHER PUBLICATIONS

WO International Search Report application No. PCT/EP2019/060976, dated Jul. 8, 2019.
(Continued)

*Primary Examiner* — Samuel S Hanna

(57) ABSTRACT

A surgical device and method for performing a controlled resection of the neck of a femur during a hip replacement procedure. The surgical device includes a body portion. The body portion has a mounting portion. The mounting portion is mountable on a femoral head of the femur to position the body portion with respect to a center of the femoral head. The body portion also has an opening for mounting the body portion on an intramedullary pin located in an intramedullary canal of the femur. The surgical device also includes a resection guide. The resection guide is adjustably locatable at a plurality of positions on the body portion for positioning a resection plane indicator of the resection guide with respect to the neck of the femur according to a measured radius/diameter of the femoral head.

6 Claims, 5 Drawing Sheets

(56) References Cited

U.S. PATENT DOCUMENTS

| | | | |
|---|---|---|---|
| 5,464,406 A | 11/1995 | Ritter et al. | |
| 5,578,037 A | 11/1996 | Sanders | |
| 5,607,431 A | 3/1997 | Dudasik et al. | |
| 6,258,097 B1 | 7/2001 | Cook et al. | |
| 6,421,630 B1 | 7/2002 | Yamada et al. | |
| 6,503,255 B1 | 1/2003 | Albrektsson | |
| 7,582,091 B2 | 9/2009 | Duncan et al. | |
| 7,601,155 B2 | 10/2009 | Petersen | |
| 7,833,275 B2 | 11/2010 | Mears et al. | |
| 8,246,621 B2 | 8/2012 | Poncet | |
| 2003/0009170 A1 | 1/2003 | Tornier | |
| 2004/0122439 A1 | 6/2004 | Dwyer | |
| 2004/0236341 A1 | 11/2004 | Petersen | |
| 2007/0162039 A1* | 7/2007 | Wozencroft | A61B 17/15 606/89 |
| 2014/0276866 A1 | 9/2014 | Endsley | |

FOREIGN PATENT DOCUMENTS

| | | |
|---|---|---|
| TW | 201540251 A | 11/2015 |
| WO | 2002/026145 A1 | 4/2002 |
| WO | 2003/009170 A1 | 1/2003 |
| WO | WO2005/110250 | 11/2005 |
| WO | 2020/001830 A1 | 1/2020 |
| WO | 2020/002190 A1 | 1/2020 |
| WO | 2020/002198 A1 | 1/2020 |

OTHER PUBLICATIONS

WO International Search Report Application No. PCT/EP2019/066612, dated Oct. 1, 2019.

WO International Search Report Application No. PCT/EP 2019/060894, dated Aug. 9, 2019.

WO International Search Report Application No. PCT/EP2019/066596, dated Oct. 7, 2019.

* cited by examiner

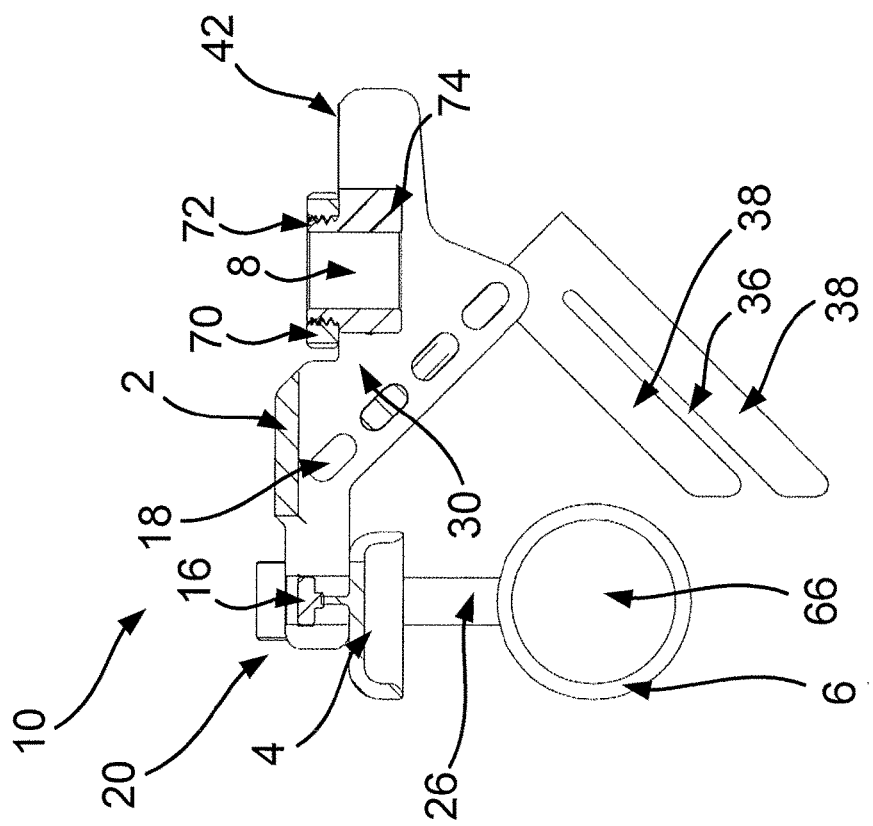
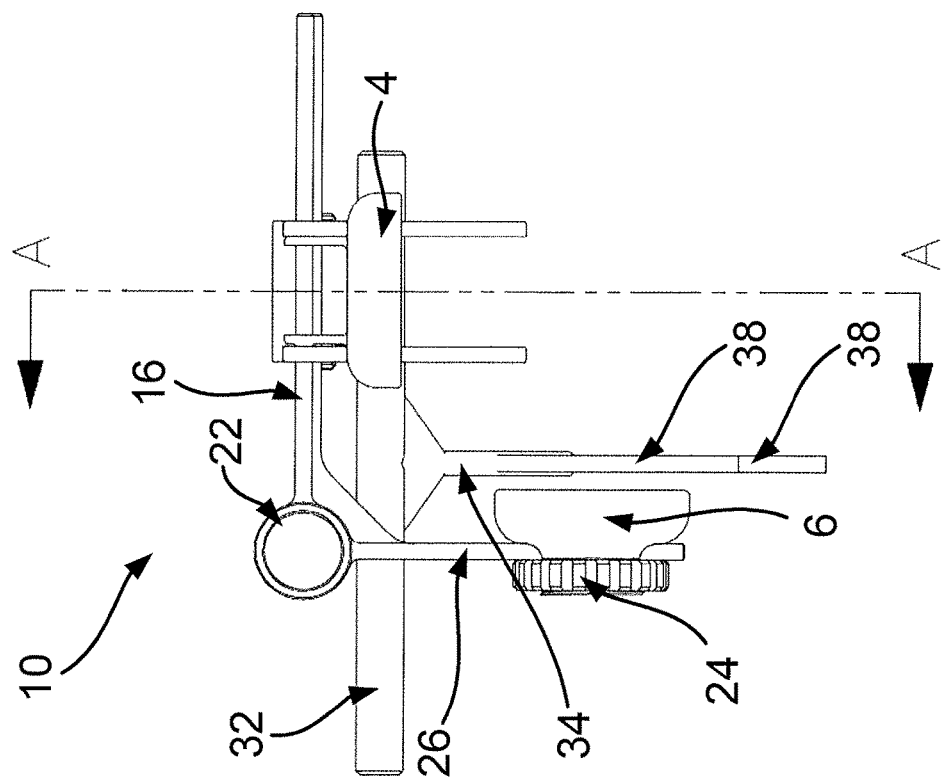
Fig. 3B
Fig. 3A

SURGICAL DEVICE AND METHOD

CROSS-REFERENCE TO RELATED APPLICATIONS

This application is a National Stage Application filed Under 35 U.S.C. § 371 of International Application No. PCT/EP2019/060976 filed Apr. 29, 2019, which claims priority to GB1810477.8 filed Jun. 26, 2018 and GB1904256.3 filed Mar. 27, 2019, which are all hereby incorporated by reference in their entireties.

FIELD OF THE INVENTION

This invention relates to a surgical device and method for performing a controlled resection of the neck of a femur during a hip replacement procedure.

BACKGROUND OF THE INVENTION

Hip replacement is a surgical procedure in which the hip joint is replaced by a prosthetic implant. Total replacement of the hip joint involves installing an acetabular cup implant in the acetabulum of a patient and installing another implant in the femur of the patient. In partial hip replacement, an implant is installed in the femur of the patient, but an acetabular cup is not installed in the acetabulum. In either type of procedure, the implant that is installed in the femur typically includes a stem, which is received in the intramedullary canal, and a head having a bearing surface which is received in the acetabulum or acetabular cup implant. The implant typically also includes a neck, which extends between a proximal end of the stem and the head.

In order to install the implant in the intramedullary canal, the neck of the femur is first resected. The resection of the femoral neck provides access to the intramedullary canal, which can then be prepared to receive the stem of the implant using broaches and reamers. During a hip replacement procedure, restoration of leg length is generally a product of good planning and experience and may generally be controlled by pre-operative planning. The neck resection may generally be a freehand cut and. A seating position of the implant, once the stem has been installed within intramedullary canal, may generally depend upon the location of the cut. If the cut is not correctly positioned, this can lead to an incorrect seating position for the implant. This can in turn adversely affect the resulting leg length of the femur with its femoral implant.

U.S. Pat. No. 6,503,255 B1 describes a cutting guide instrument and method for enabling high-precision resection of the head of the neck of a human femur at a predetermined cutting angle to the femoral shaft and on a predetermined cutting level with respect to the proximal end of the caput. A support part is fixed to the femur during the resection. A longitudinal guide carrier is supported by the support part and is aligned along the femoral collum at said predetermined cutting angle to the femoral shaft. A cutting guide is supported by and movable along the axis of the guide carrier to a cutting position corresponding to the predetermined cutting level.

WO 2002/026145 A1 describes a guiding instrument for the resection of a femoral neck in connection with total hip replacement, said guiding instrument comprising an instrument body having means for receiving a shank or the like that is mounted in the medullary canal of the femoral neck, said shank having a longitudinal centre axis the instrument body being displacable along said shank, and a guiding means having a guiding arrangement for the means that perform cutting of the femoral neck. At least a rotation ruler is attached to the instrument body, said rotation ruler being intended to cooperate with the existing femoral head of the femur.

U.S. Pat. No. 5,578,037 A describes a surgical resection guide that enables a surgeon to resect a femoral neck, during a hip arthroplasty procedure, such that a femoral prosthesis can be implanted within a patient to preserve or closely approximate the anatomic center of rotation of the hip. The guide is able to be used for left or right hip arthroplasty procedures, with either anterior or posterior surgical approaches.

U.S. Pat. No. 8,246,621 B2 describes an instrument kit is provided for reaming bone around a head of a bone, the bone including an implanted epiphysis component. The instrument kit includes a reaming guide and a reamer. The reaming guide is couplable to the epiphysis component and has a first reamer support feature and a second reamer support feature. The reamer is couplable to one of the first reamer support feature and the second support feature to ream bone around the epiphysis component.

U.S. Pat. No. 7,601,155 B2 describes an intramedullary femoral broach that aligns two instruments. A femoral neck resector guide slides over the broach and centers on the patient's femoral head to determine the height and angular rotation of resection. A circular ring of the head and cutting arms assure the system will fit any femur. A template is applied to the femoral broach and seats itself against the buttress of the broach locking it into place. The broach is then reinserted into the intramedullary canal. When the template reaches the greater trochanter the sizer is adjusted to the rotational anteversion of the canal. The handle of the femoral broach is struck with a mallet until the template is imbedded into the proximal femoral neck intramedullary bone. A retractor facilitates reaming of the acetabulum through a small anterior incision. A proximal portion digs into the bone of the superior acetabulum to allow for retraction of soft tissues.

U.S. Pat. No. 4,959,066 A describes an osteotomy guide assembly for femoral neck osteotomy includes a saddle locator assembly and a saw guide attachment. The saddle locator assembly includes a barrel-shaped locating device that locates the saddle region of the proximal femur. The barrel further includes a transverse support bar extending from the barrel. The barrel is positioned over an intramedullary shaft which is temporarily positioned in and extends from the medullary canal of the femur. A saw guide is used in conjunction with the saddle locator assembly. The saw guide is attached to the support bar by a single locking means which provides for positional adjustment of the saw guide relative to the support bar in two directions, including adjustment in the anterior-posterior direction along the transverse support bar and axially along the femur via a post which extends from the saw guide.

U.S. Pat. No. 7,833,275 B2 describes a method and apparatus for performing a minimally invasive total hip arthroplasty. An approximately 3.75-5 centimeter (1.5-2 inch) anterior incision is made in line with the femoral neck. The femoral neck is severed from the femoral shaft and removed through the anterior incision. The acetabulum is prepared for receiving an acetabular cup through the anterior incision, and the acetabular cup is placed into the acetabulum through the anterior incision. A posterior incision of approximately 2-3 centimetres (0.8-1.2 inches) is generally aligned with the axis of the femoral shaft and provides access to the femoral shaft. Preparation of the femoral shaft including the reaming and rasping thereof is performed through the posterior incision, and the femoral stem is inserted through the posterior incision for implantation in the femur. A variety of novel instruments including an osteotomy guide; an awl for locating a posterior incision aligned with the axis of the femoral shaft; a tubular posterior retractor; a selectively lockable rasp handle with an engagement guide; and a selectively lockable provisional neck are utilized to perform the total hip arthroplasty.

U.S. Pat. No. 5,607,431 A describes a surgical instrument system for preparing the medullary canal of the femur for implanting a prosthetic femoral component includes a template to be used in determining osteotomy position from an x-ray. A gauge is provided to locate and mark this position on the anterior femur. A distal reamer having an elongated drive shaft is used to form the canal to receive the distal stem of the femoral component. A metaphyseal template is used to determine the proper anteversion/retroversion and a chisel is used to cut the lateral area of the femur, both of which are guided by the elongated reamer shaft. A proximal broach also guided by the reamer shaft is used to shape the proximal medullary canal.

U.S. Pat. No. 7,582,091 B2 describes an osteotomy guide for indicating the femoral neck resection on a femur and its method of use are presented. The osteotomy guide includes an indexing feature for aligning the guide with an anatomic landmark and a resection guide for indicating the resection relative to the indexing feature.

U.S. Pat. No. 4,621,630 A describes a guide for femoral neck osteotomy that comprises a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongate planar surface disposed at an angle of 45 DEG to the axis of the rod. In use, the rod is aligned with the long shaft axis of the femur and attached to the femur at the greater trochanter. The rod is manipulated until the support arm and the long shaft axis of the tibia are disposed in the same plane. This procedure properly positions the elongate planar surface of the guide bar whereby an instrument in engagement with that surface traverses the femoral neck at an angle of 45 DEG to the long shaft axis of the femur.

US 2004/236341 A1 describes a minimally invasive surgical procedure for total hip surgery that features four unique instruments that facilitate the procedure. A manual Intramedullary Femoral Broach facilitates axial alignment of the subsequent two instruments that attach to it for alignment and stability. The Femoral Neck Resector Guide slides over the proximal portion of the Broach and self centers on the patient's femoral head to determine the height and angular rotation of resection of the femoral neck. The circular ring of the head locator and the cutting arms assure that the system will fit any size femur. The Sizer/Cutter Template is applied to the Femoral Broach from the tip with the tip removed from the intermedullary canal and seats itself firmly against the Femoral Broach raised buttress locking it into place. The Femoral Broach is then is reinserted into the intramedullary canal. When the Sizer/Cutter Template reaches the greater trochanter the Sizer is adjusted to the rotational anteversion of the canal. The handle of the Femoral Broach then is struck with a mallet until the Sizer/Cutter Template is imbedded into the proximal femoral neck intramedullary bone. The right angled Anterior Acetabulum Retractor is elongated to facilitate reaming of the acetabulum through a small anterior incision. A broadened curved proximal portion has angulated teeth that dig into the bone of the superior acetabulum to provide the fulcrum for retraction of the overlying soft tissues.

EP 1 797 834 A1 describes an alignment guide for use in femoral head surgery comprising: a support member; a cannulated rod supported by, and adjustable with respect to, the support member; and a locator arm having a proximal end connected to the support member and a distal end having location means for location on a high point of the femoral head and a notch guard which in use will extend around at least a part of the femoral neck.

US 2003/009170 A1 describes an ancillary tool that comprises a guide for cut-out of the ulna and/or the radius intended to be positioned with respect to a trial humeral trochlea belonging also to said ancillary tool and representative of the anatomical humeral trochlea when this trial trochlea is in place with respect to the corresponding cubital and/or radial articular surfaces. This guide is also adapted to be positioned with respect to the ulna and/or to the radius equipped with this trial trochlea.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a surgical device for performing a controlled resection of the neck of a femur during a hip replacement procedure, the surgical device comprising:
 a body portion comprising:
  a mounting portion, wherein the mounting portion is mountable on a femoral head of the femur to position the body portion with respect to a center of the femoral head; and
  an opening for mounting the body portion on an intramedullary pin located in an intramedullary canal of the femur; and
 a resection guide, wherein the resection guide is adjustably locatable at a plurality of positions on the body portion for positioning a resection plane indicator of the resection guide with respect to the neck of the femur according to a measured radius/diameter of the femoral head.

A device according to embodiments of this invention can aid in indicating a correct position of the neck resection plane, for restoring the leg length and/or femoral offset in a hip replacement procedure. Embodiments of this invention achieve this by providing a body portion that can be mounted on the femur using an intramedullary pin located in the intramedullary canal of the femur to create an extramedullary reference to the intramedullary axis and a mounting portion to reference the center of the femoral head. A resection guide can then be positioned on the body portion according to a measured radius/diameter of the femoral head. Typically, for a larger measured size of the femoral head, the resection guide can be positioned on the body portion such that the resection plane indicator is located further away from the (reference taken by) the mounting portion.

The body portion can include a plurality of discrete connection features, each discrete connection feature for mounting the resection guide on the body portion to place the resection plane indicator at a respective position according to the measured radius/diameter of the femoral head.

This provides a convenient way of mounting the resection guide in according to the measured radius/diameter of the femoral head, for correctly indicating the resection plane.

The body portion can include a connection feature for mounting the resection guide on the body portion. A position of the connection feature can be slideably adjustable within the body portion for continuously positioning resection plane indicator of the resection guide according to the measured radius/diameter of the femoral head. This provides another convenient way of mounting the resection guide in according to the measured radius/diameter of the femoral head, for correctly indicating the resection plane. The slideably adjustable connection feature can allow for more accurate positioning of the resection guide.

The or each connection feature can include an opening in the body portion within which a mounting member of the resection guide is receivable. This can provide a robust and secure mounting for the resection guide.

The resection guide can be removably mountable on the body portion. This can allow the body portion to be manipulated more easily while mounting it in the femur, prior to attaching the resection guide.

The mounting portion can be mountable on an anterior aspect of the femoral head.

The surgical device can include a second mounting portion. The second mounting portion can be mountable on a superior aspect or on a superior lateral aspect of the femoral head while the anteriorly mountable mounting portion is mounted on the anterior aspect of the femoral head. The provision of two mounting portions can allow the body portion to be mounted more securely and accurately on the femur. The superior aspect of the femoral head is a common area for wear and tear in the femur. For this reason, mounting portions mounted on the anterior and/or superior lateral aspects may provide a more accurate reference to the femoral head center.

The anteriorly mountable mounting portion can be adjustably positionable with respect to a remainder of the body portion in a direction parallel to an intramedullary axis of the femur according to a radius/diameter of the femoral head of the femur.

The body portion can include markings for reading off the radius/diameter of the femoral head according to the position of the anteriorly mountable mounting portion with respect to the remainder of the body portion. The value that is read off can be used to determine the type of neck/head combination that is used in the implant, for restoring the leg length and/or femoral offset of the femur.

The mounting portion can be mountable on a superior aspect or on a superior lateral aspect of the femoral head.

The resection plane indicator can include a guide slot or a guide surface.

The guide slot or guide surface can be a cutting slot or a cutting guide surface for receiving a blade of a cutting device during the resection of the neck.

The opening for mounting the body portion on the intramedullary pin can be adjustably positionable within the body portion according to a femoral offset of the femur.

The body portion can include markings for reading off the femoral offset of the femur according to the position of the opening for mounting the body portion on the intramedullary pin, while the or each mounting portion is mounted on the femoral head. The femoral offset value that is read off can be used to determine the type of neck/head combination that is used in the implant, for restoring the femoral offset.

The or each mounting portion may include a substantially circular femoral head contacting surface.

The mounting portion(s) may be referred to by those skilled in the art as spherometer(s).

According to another aspect of the invention, there is provided a method for performing a controlled resection of the neck of a femur during a hip replacement procedure using a surgical device comprising:
 a body portion comprising:
  a mounting portion, wherein the mounting portion is mountable on a femoral head of the femur to position the body portion with respect to a center of the femoral head; and
  an opening for mounting the body portion on an intramedullary pin located in an intramedullary canal of the femur; and
 a resection guide, wherein the resection guide is adjustably locatable at a plurality of positions on the body portion for positioning a resection plane indicator of the resection guide with respect to the femur according to a measured radius/diameter of the femoral head,
the method comprising:
 mounting the body portion on an intramedullary pin located in an intramedullary canal of the femur by inserting the pin into the opening in the body portion;
 mounting the mounting portion on the femoral head;
 locating the resection guide on the body portion for positioning the resection plane indicator with respect to the femur according to a measured radius/diameter of the femoral head; and
 using the resection plane indicator to either:
  mark the position of the resection plane on the neck of the femur; or
  guide a blade of a cutting device to resect the neck of the femur.

A method according to embodiments of this invention can aid in indicating a correct position of the neck resection plane, for restoring the leg length and/or femoral offset in a hip replacement procedure. Embodiments of this invention achieve this by providing a body portion that can be mounted on the femur using an intramedullary pin located in the intramedullary canal of the femur to create an extramedullary reference to the intramedullary axis and a mounting portion to reference the center of the femoral head. A resection guide can then be positioned on the body portion according to a measured radius/diameter of the femoral head. Typically, for a larger measured size of the femoral head, the method can include positioning the resection guide on the body portion such that the resection plane indicator is located further away from the (reference taken by) the mounting portion.

The method may include measuring the radius/diameter of the femoral head. This may be done using callipers or such like, and/or may be done using features of the device itself.

The method can include mounting the resection guide on the body portion using one of a plurality of discrete connection features of the body portion to place the resection plane indicator according to the measured radius/diameter of the femoral head. This is a convenient way of mounting the resection guide in according to the measured radius/diameter of the femoral head, for correctly indicating the resection plane.

The method can include: mounting the resection guide on the body portion using a connection feature of the body portion; and slideably adjusting a position of the connection feature within the body portion to place the resection plane indicator according to the measured radius/diameter of the femoral head. This is another convenient way of mounting the resection guide in according to the measured radius/diameter of the femoral head, for correctly indicating the resection plane. The slideably adjustable connection feature can allow for more accurate positioning of the resection guide.

The method can include mounting the mounting portion on an anterior aspect of the femoral head.

The method can include mounting a second mounting portion of the surgical device on a superior aspect or on a superior lateral aspect of the femoral head. The use of two mounting portions can allow the body portion to be mounted more securely and accurately on the femur. The superior aspect of the femoral head is a common area for wear and tear in the femur. For this reason, using mounting portions mounted on the anterior and/or superior lateral aspects may provide a more accurate reference to the femoral head center.

The method can include adjusting the position of the anteriorly mounted mounting portion with respect to a remainder of the body portion in a direction parallel to an intramedullary axis of the femur according to the radius/diameter of the femoral head of the femur.

The method can include reading off the radius/diameter of the femoral head using markings on the body portion according to the position of the anteriorly mounted mounting portion with respect to the remainder (e.g. a second mounting portion) of the body portion.

The method can include mounting the mounting portion on a superior aspect or on a superior lateral aspect of the femoral head.

The method can include adjustably positioning the opening for mounting the body portion on the intramedullary pin with respect to the remainder of the body portion according to a femoral offset of the femur.

The method can include reading off the femoral offset of the femur according to the position of the opening for mounting the body portion on the intramedullary pin with respect to the remainder of the body portion according to a femoral offset of the femur, while the or each mounting portion is mounted on the femoral head.

The method can include using the radius/diameter of the femoral head and/or femoral offset values read off from the surgical device to determine a leg length and/or femoral offset of a femoral implant to be installed in the hip replacement procedure.

The method can include inserting the intramedullary pin into the intramedullary canal of the femur prior to mounting the body portion on the intramedullary pin.

The or each mounting portion may include a substantially circular femoral head contacting surface.

The mounting portion(s) may be referred to by those skilled in the art as spherometer(s).

BRIEF DESCRIPTION OF THE DRAWINGS

Embodiments of the present invention will be described hereinafter, by way of example only, with reference to the accompanying drawings in which like reference signs relate to like elements and in which:

FIG. 3A shows a medial view of the device of FIG. 1;

FIG. 3B shows a cross section of the device of FIG. 1 through the line A-A in FIG. 3A;

DETAILED DESCRIPTION

Embodiments of the present invention are described in the following with reference to the accompanying drawings.

Figure 1:
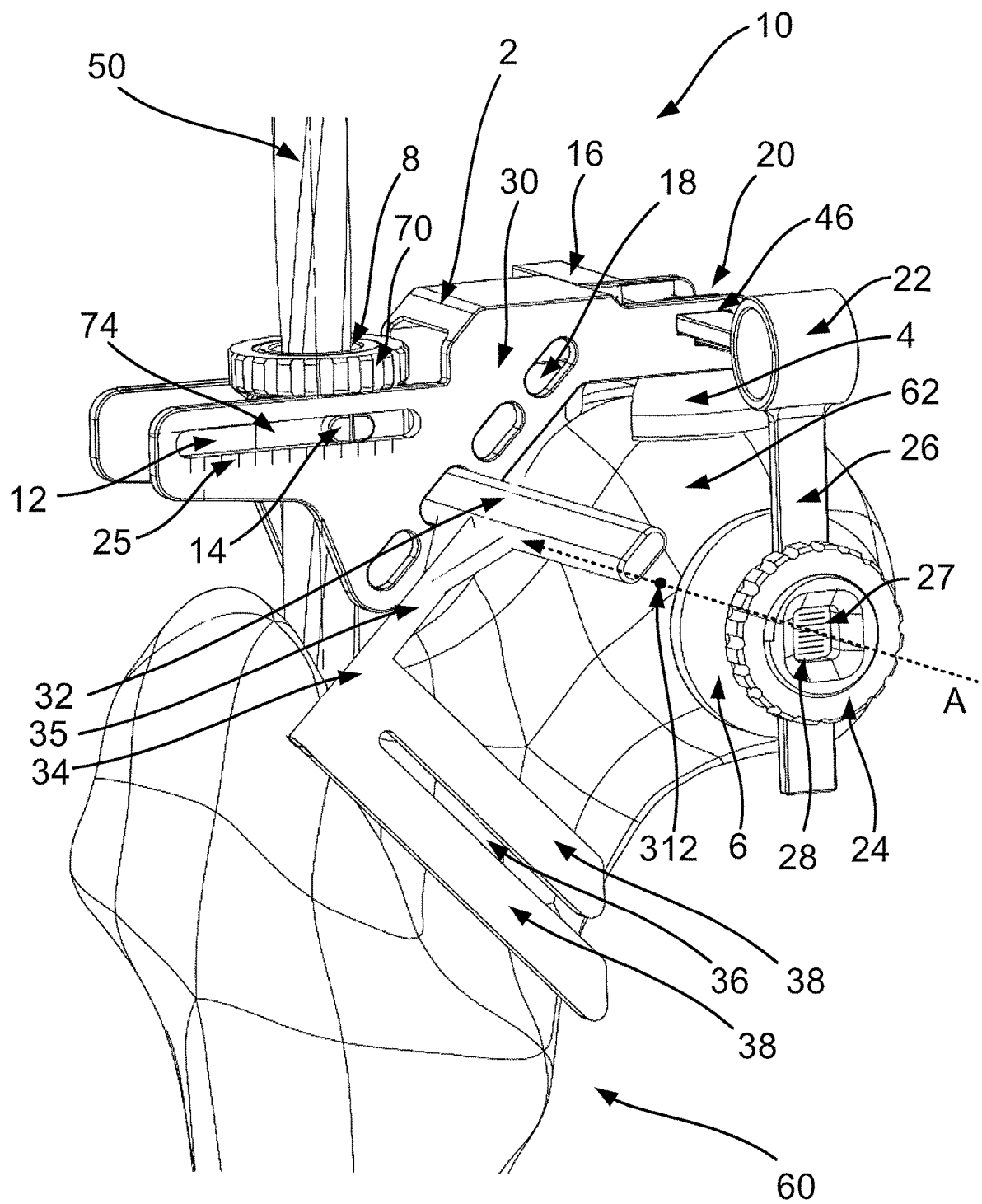
FIG. 1 shows a device mounted on a femur according to an embodiment of this invention.
Figure 2:
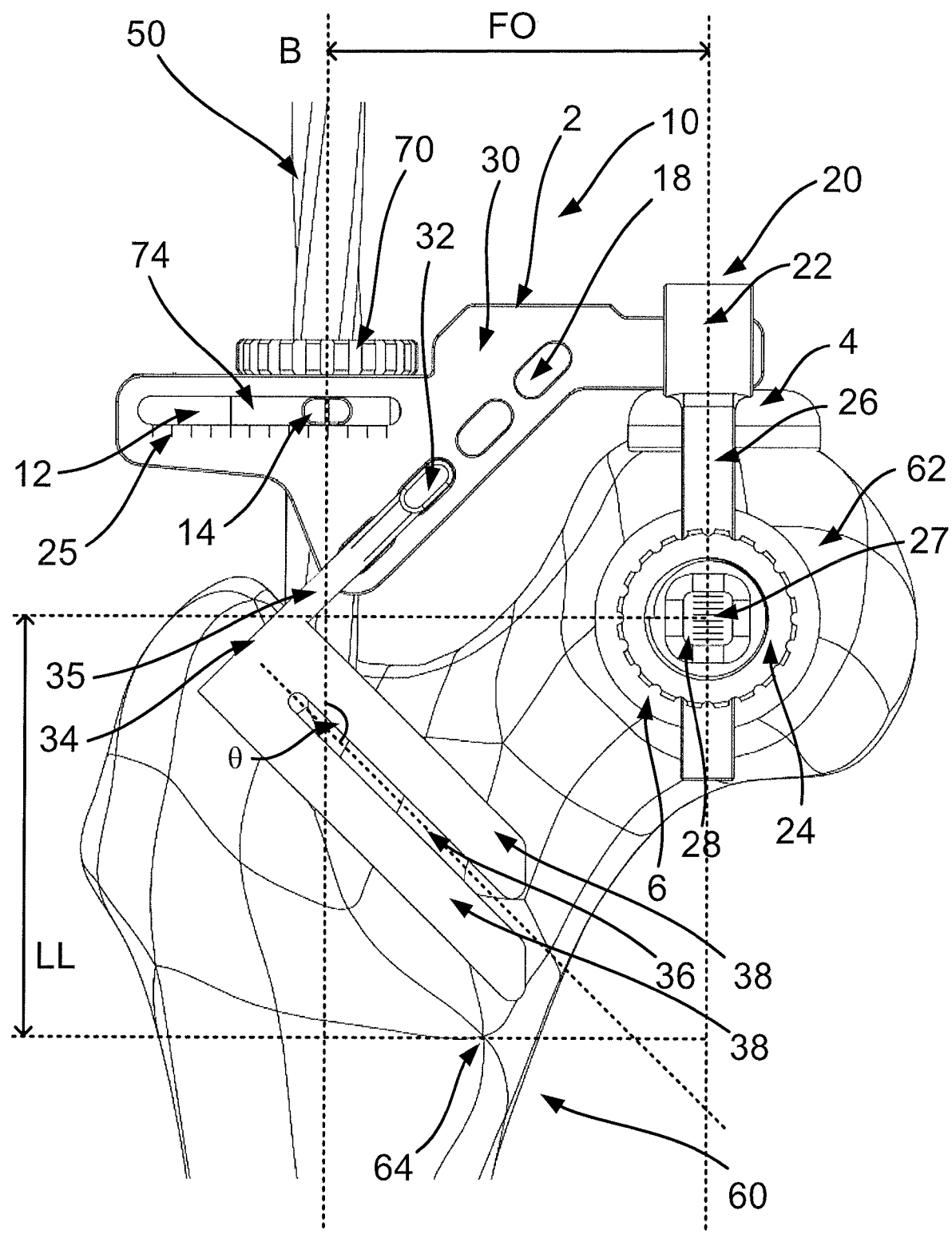
FIG. 2 shows an anterior view of the device of FIG. 1 mounted on a femur.
Figure 4:
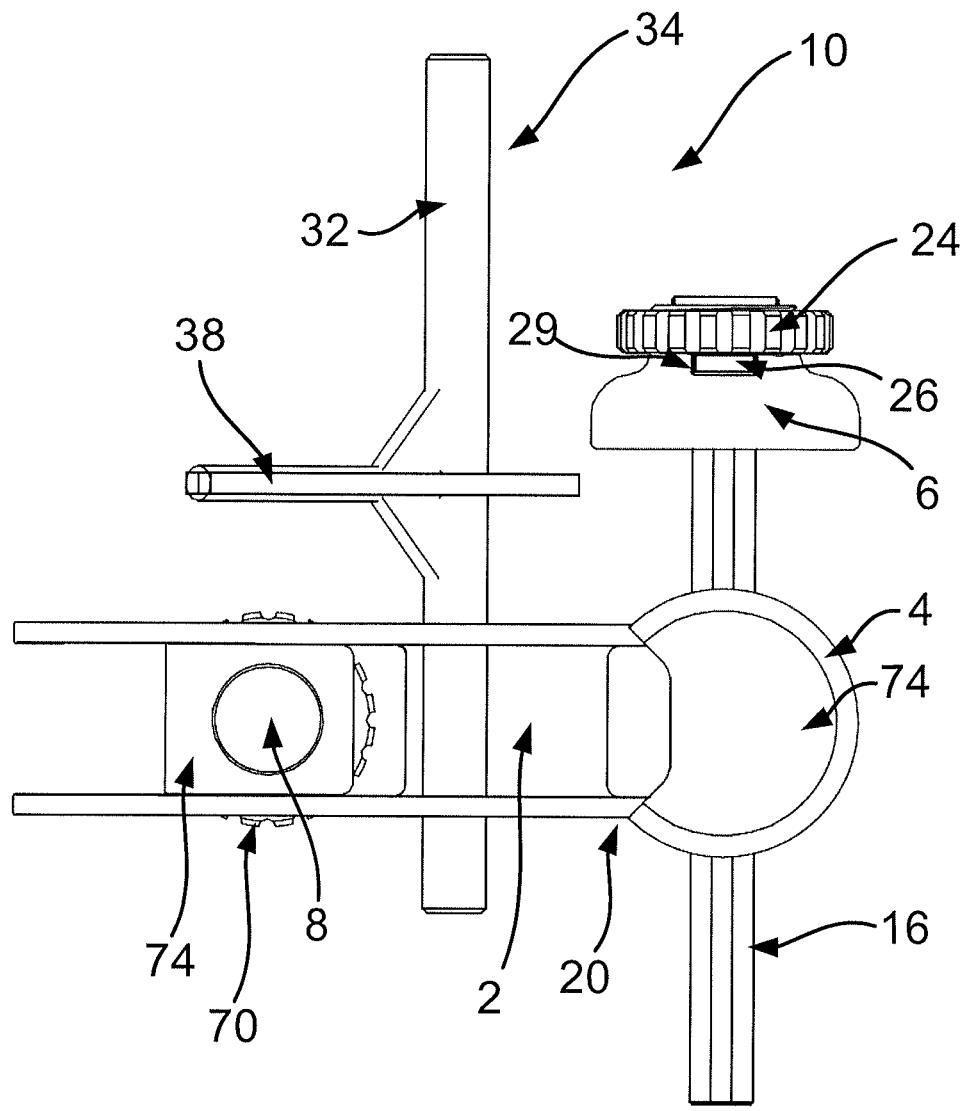
FIG. 4 shows an inferior view of the device of FIG. 1.

FIG. 1 shows a surgical device 10 mounted on a femur according to an embodiment of this invention. FIGS. 2, 3A and 4 show anterior, medial and inferior views of the device 10 of FIG. 1. FIG. 3B shows a cross section of the device of FIG. 1 through the line A-A in FIG. 3A. The surgical device 10 in FIGS. 1 to 4 can be used to perform a controlled resection of the neck of a femur during a hip replacement procedure.

The device 10 includes a body portion 2. The body portion 2 includes a mounting portion 6. The mounting portion 6 may be referred to by those skilled in the art as a spherometer. The mounting portion 6 includes a femur facing surface 66. The femur facing surface may be substantially concave and curved (see integer 66 in FIG. 3B) so as to fit against the femoral head 62. The mounting portion 6 may include a substantially circular femoral head contacting surface. For example, as shown in FIG. 3B, a rim of the femur facing surface 66 may be substantially circular, for resting against the femoral head 62. In some embodiments, the femur facing surface 66 may comprise a ring, which forms a substantially circular femoral head contacting surface, which can rest against the femoral head 62. The mounting portion 6 may thus be removably mounted on the femoral head 62. The other mounting portions described herein may be shaped and configured in the same way as described above in relation to the mounting portion 6.

During the hip replacement procedure, the surgeon may mount the mounting portion 6 on the anterior aspect of the femoral head 62 such that a central axis of the mounting portion 6 (see the dotted arrow labelled A in FIG. 1) is aligned with the femoral head center 312 when viewing the femoral head 62 from an anterior position. This may generally be achieved by visual inspection of the anterior aspect of the femur 60 and femoral head 62 while manually positioning the mounting portion 6. The mounting of the mounting portion 6 on the femoral head in this way positions the body portion 2 with respect to femoral head center 312.

In some embodiments, as shown in the Figures, the body portion 2 may include a second mounting portion 4. The second mounting portion 4 may be referred to by those skilled in the art as a spherometer. The second mounting portion 4 in the present embodiment is positioned on an underside (inferiorly facing side) of the body portion 2 so that it can be mounted on a superior aspect of the femoral head 62 while the anteriorly mountable mounting portion 6 is mounted on the anterior aspect of the femoral head 62. The second mounting portion 4 also includes a femur facing surface. The femur facing surface may be substantially concave and curved (see integer 74 in FIG. 4) so as to fit against the femoral head 62. The second mounting portion 4 may include a substantially circular femoral head contacting surface. For example, as shown in FIG. 4, a rim of the femur facing surface 74 may be substantially circular, for resting against the femoral head 62. In some embodiments, the femur facing surface may comprise a ring, which forms a substantially circular femoral head contacting surface, which can rest against the femoral head 62. The second mounting portion 4 may thus also be removably mounted on the femoral head 62.

The second mounting portion 4 can assist in the correct positioning of the body portion 2 with respect to the femoral head center 312. The second mounting portion 4 can also allow for a more secure mounting of the device 10 on the femoral head 60 while the device 10 is being used. The superior aspect of the femoral head 60 is a common area for wear and tear in the femur. Accordingly, it is also envisaged that a second mounting portion of the device could instead be positioned on the body portion 2 so that it can be mounted on the superior lateral aspect of the femoral head 62 while the anteriorly mountable mounting portion 6 is mounted on the anterior aspect of the femoral head 62 (see the embodiment of FIG. 5, to be described in more detail below).

The device 10 also includes a resection guide 34. The resection guide includes a resection plane indicator for indicating a resection plane on the neck of the femur 60. In the present embodiment, the resection plane indicator of the resection guide 34 comprises a guide slot 36. The guide slot 36 may defined by a pair of jaws 38. The resection plane indicated by the guide slot 36 when viewed from an anterior position of the femur 60, may extend at an angle θ with respect to the intramedullary axis of the femur 60 (see the dotted line labelled B in FIG. 2). The angle θ may, for instance, be around 127°, 129° or 135°.

The resection plane indicator may alternatively comprise a guide surface. For instance a peripheral edge of the resection plane indicator may a substantially flat surface for indicating the resection planes.

The guide slot 36 (or the guide surface) may be used to mark the resection plane using a pen or scribe or such like. The guide slot 36 (or the guide surface) may also be used as a cutting slot or a cutting guide surface for receiving a blade of a cutting device during resection of the neck of the femur 60.

In the present embodiment, the resection guide 34 includes a first arm 32 which, with the mounting portion 6 mounted on the anterior aspect of the femoral head 62 as described above, may extend anteriorly outwardly from the body portion 2. The resection guide 34 also includes a second arm 35, which may extend substantially perpendicularly to the first arm 32, and generally towards the intramedullary axis B when viewed from an anterior position of the femur 60. The pair of jaws 38 may extend from the second arm 34 so as to define the guide slot 36 as described above.

With reference to FIG. 2, for the purpose of this disclosure, the leg length (LL) of the femur 60 may be defined as the distance between the lesser trochanter 64 and the femoral head center, along a direction parallel to the intramedullary axis B. Again with reference to FIG. 2, for the purpose of this disclosure, the femoral offset of the femur 60 may be defined as the distance between the femoral head center and the intramedullary axis B, in a direction perpendicular to the intramedullary axis B.

During the hip replacement procedure, the size (e.g. diameter/radius) of the femoral head 62 can be measured. This may be done using callipers or such like, or can be done using features of the device 10 itself (e.g. the scale 27 to be described below). The resection guide 34 is adjustably locatable at a plurality of positions on the body portion 2 for positioning the resection plane indicator of the resection guide 34 with respect to the neck of the femur according to a measured radius/diameter of the femoral head 62. The resection plane indicator can accordingly be positioned using the femoral head center 312 as a reference, and at a distance from the femoral head center that is determined by the measured size of the femoral head 62. Typically, for a larger measured size of the femoral head 62, the resection guide 34 can be positioned on the body portion 2 such that the resection plane indicator is located further away from the (reference taken by) the mounting portion(s) 6, 4. In this way, the location of the resection plane(s) can be determined in a controlled manner. This in turn means that the seating position of the implant, once the stem of the implant has been installed within intramedullary canal, may be controlled. This can facilitate restoration of the leg length and/or femoral offset of the resulting femur 60 with its femoral implant particularly, but not necessarily exclusively, when using an implant system in which the neck length of the implant is constant.

The adjustable location of the resection guide 34 on the body portion 2 for correctly positioning the resection plane indicator can be implemented in a number of ways.

The body portion 2 may, for instance, include a plurality of discrete connection features, each discrete connection feature for mounting the resection guide 34 on the body portion 2 to place the resection plane indicator at a respective position according to the measured radius/diameter of the femoral head. In the present embodiment, these discrete connection features are implemented as openings 18 in an anterior face 30 of the body portion 2. Each opening 18 is sized and shaped snugly to receive an end of the first arm 32, which forms a mounting member of the resection guide 34. As can be seen in FIG. 4, a posterior face of the body portion 2 may be provided with corresponding openings, whereby the first arm 32 can be passed completely though the body portion 2, for a more secure mounting of the resection guide 34. It is envisaged that the connection arrangement between the first arm 32 and the openings 18 could be reversed for instance the body portion may include a plurality of pegs located anterior face 30, for receipt in an opening located on the end of the first arm 32.

The openings 34 may be distributed in a row on the body portion 2. As is most clearly seen in FIG. 2, the row may be oriented in a direction substantially perpendicular to the resection plane indicated by the resection guide. Although in the present embodiment, the device 10 includes four discrete connection features, it is envisaged that greater or fewer such discrete connection features may be provided.

Another example of the implementation of the adjustable location of the resection guide 34 on the body portion 2 for correctly positioning the resection plane indicator will be described below in relation to the embodiment of FIG. 5.

In some embodiments, the body portion 2 can assist in the correct positioning of the mounting portion(s) 6, 4 on the femoral head 62 and can also allow measurements of the femoral offset to be taken.

In the present embodiment, the body portion 20 includes an opening 8 for mounting the body portion 2 on an intramedullary pin 50 located in an intramedullary canal of the femur 60. The intramedullary pin 50 can be inserted into the intramedullary canal prior to mounting the body portion 2 on the femur 60, to provide an extramedullary reference to the intramedullary axis B. The intramedullary pin 50 can, for instance, comprise and initiation rod or reamer. The mounting of the body portion 2 in this way can allow the body portion 2 to be positioned with respect to both the extramedullary reference to the intramedullary axis B that is provided by the intramedullary pin 50 and the reference to the femoral head center 312 that is provided by the mounting portion(s) 6, 4. The mounting of the body portion 2 in this way can also provide additional stability for keeping the mounting portion(s) 6, 4 and body portion 2 in position e.g. while using the resection guide 34 and/or taking the readings described below.

The opening 8 may, for instance, comprise an aperture that passes through the body portion 22 (as shown in the Figures). Alternatively, the opening 8 may comprise a recess on the body portion, within which the intramedullary pin 50 may be received. The body portion 2 may be provided with a means for fixing and retaining the intramedullary pin 50 in the opening 8. For instance, in the present embodiment, the opening 8 is provided with a split bushing 72 (see FIG. 3B) with an external thread, upon which a ring 70 having an internal thread is mounted. By rotating the ring 70, the split bushing 72 may be urged against the intramedullary pin 50, to fix the position of the body portion 2 relative to the intramedullary pin 50, once the body portion and mounting portion(s) 6, 4 have been placed on the femur 60.

The position of the opening 8 may be adjustably positionable within the body portion 2, according to the femoral offset of the femur 60. This can allow the body portion 2 to be adjusted so that it fits correctly on the intramedullary pin 50 with the mounting portion(s) 6, 4 mounted on the anterior aspect of the femoral head 62 as described above. The body portion 2 may also include markings 25 for reading off the femoral offset of the femur 60 according to the position of the opening 8 relative to the mounting portion(s) 6, 4, while the mounting portion(s) 6, 4 are mounted on the femoral head 62. In the present embodiment, this is implemented by providing the opening 8 through a slideable member 74, which is slideably mounted within the body portion 2. The slideable member 74 may include peg(s) 14, which are slideably received within a slot 12 located on the anterior face 30 (and optionally also a posterior face) of the body portion 2. The slot 12 may extend in a lateral-medial direction on the body portion 2. The slot 12 may be provided with the aforementioned markings 25 for reading off the femoral offset of the femur 60 by inspecting the position of the peg 14 within the slot 12.

The body portion 2 also includes a slideably adjustable arm, upon which the mounting portion 6 is slideably mounted. The arm in this embodiment is substantially L-shaped and includes an elbow 22, which may also serve as a handle for adjusting the position of the arm relative to the remainder of the body portion 2.

The mounting portion 6 is slideably mounted on a first part 26 of the arm. When the mounting portion 6 is mounted on the femoral head 62 as noted above, the first part 26 of the arm extends substantially parallel to the intramedullary axis B. The first part 26 of the arm may pass through an opening 29 in the mounting portion 6 to allow the mounting portion 6 to be slid back and forth on the first part 26 of the arm. The mounting portion 6 may be provided with an internally threaded ring 24 that can be rotated onto a corresponding thread on the mounting portion 6, to urge against the first part 26 of the arm, so as to lock down the mounting portion 6 relative to the first part 26 of the arm.

The mounting portion 6 may include a window 28 through which markings 27 located on the first part 26 of the arm may be viewed. These markings 27 can be used to read off the size (diameter/radius) of the femoral head (the markings 27 can denote the distance between the femoral head center 312 and the second mounting portion 4, assuming that the mounting portion 6 is correctly aligned with the femoral head center 312 as described above).

The arm also includes a second part 16. The second part 16 of the arm may extend substantially parallel to the central axis A of the mounting portion 6. The second part 16 of the arm is slideably received in a slot 46 in the body portion 2. This can allow the arm (and consequently, the mounting portion 6) to be moved back and forth in a posterior/anterior direction for accommodating differently sized of femoral heads 62, to position the mounting portion 6 with respect to the remainder of the body portion 2, so that the mounting portion 6 can be mounted on the anterior aspect of the femoral head 62 with the intramedullary pin 50 received in the opening 8 (and with the second mounting portion 4, if included in the device 10, is mounted on the femoral head). The movement of the second part 16 of the arm in this way can also allow adjustment of the position of the mounting portion 6 such that the device 10 to be used on either leg of the patient.

The implant that is to be installed in the femur 60 may generally include a stem, which is to be received in the intramedullary canal, and a head having a bearing surface which is to be received in the acetabulum or acetabular cup implant. The implant may typically also includes a neck, which extends between a proximal end of the stem and the head. The stem and neck may be integrally formed. The head may be attachable to the end of the neck. The readings taken using the markings 25 and/or 27 can be used to inform the choice of head that is used, for restoring the femoral offset.

Figure 5:
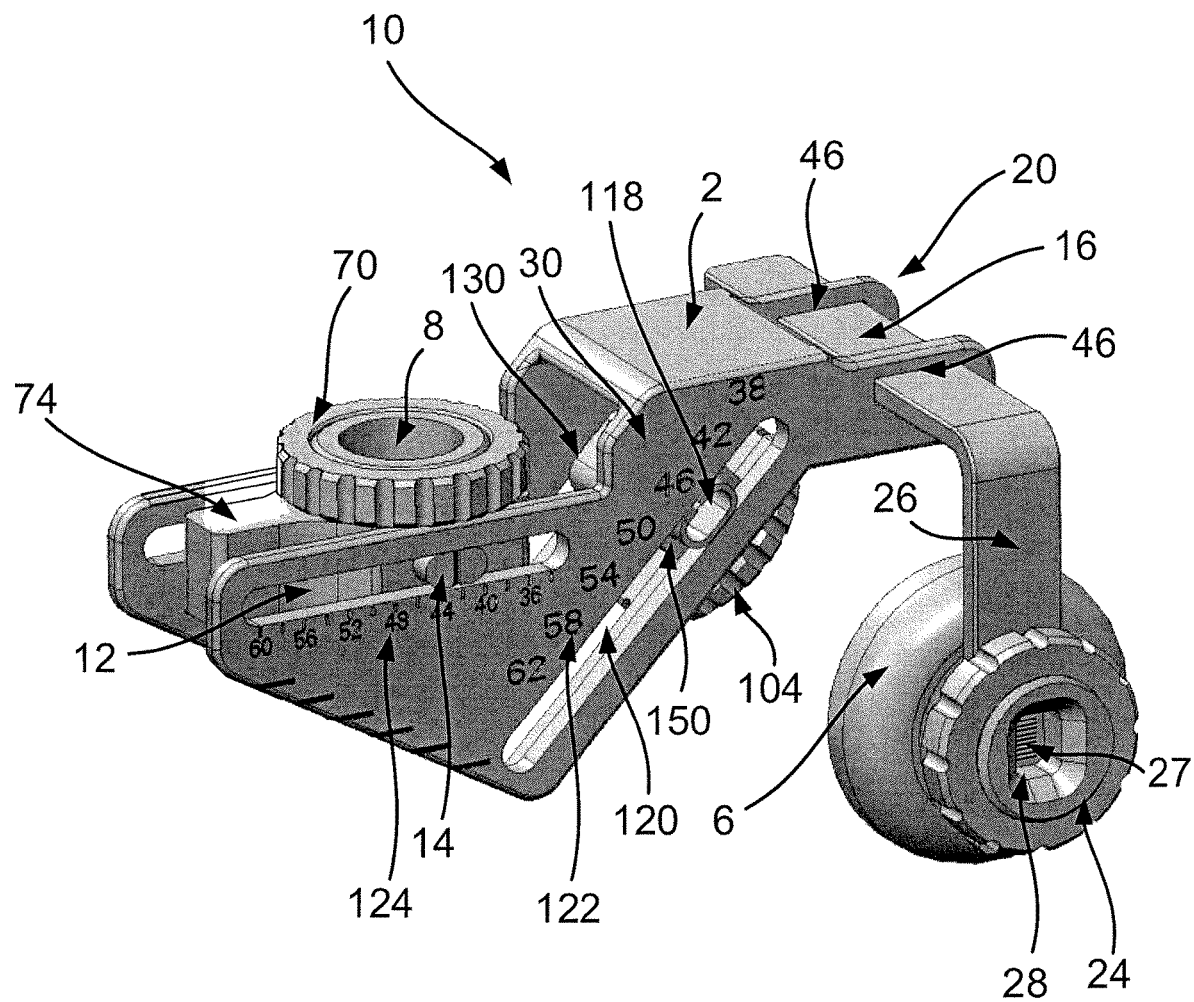
FIG. 5 shows a device according to another embodiment of this invention.

FIG. 5 shows a surgical device 10 according to another embodiment of this invention. The surgical device 10 in FIG. 5 can be used to perform a controlled resection of the neck of a femur during a hip replacement procedure. The device 10 in FIG. 5 is similar in some respects to the device 10 of FIGS. 1 to 4, and only the significant differences will be described below in detail.

In the present embodiment, the second mounting portion 104 is again located on an underside of the body portion 2, but is positioned and oriented to be mounted on the superior lateral aspect of the femoral head 62, while the anteriorly mountable mounting portion 6 is mounted on the anterior aspect of the femoral head 62. As with the embodiment of FIGS. 1 to 4, the mounting portions 6, 104 in the embodiment of FIG. 5 may be referred to by those skilled in the art as spherometer(s).

As explained previously, the superior aspect of the femoral head 60 is a common area for wear and tear in the femur. This may prevent a device 10 having a superiorly mounted second mounting portion 6 from being used effectively (e.g. the distance from the surface of the superior aspect of the femoral head 62 and the femoral head center 312 may differ from the healthy value). A device 10 having a second mounting portion 104 that is positioned for superior lateral mounting may thus be used for patients that have a significant amount of such wear and tear. The configuration of the arm upon which the mounting portion 6 is mounted may be substantially the same as described above in relation to FIGS. 1 to 4. The scale 27 can still use the relative position of the central axis A of the mounting portion 6 and the second mounting portion 104 for determining the size of the femoral head 62.

Although the resection guide of the present embodiment is not shown in FIG. 5, it may be a resection guide substantially as described above in relation to FIGS. 1 to 4. In the present embodiment, the connection of the resection guide to the body portion 2 is implemented in the form of a slideable member 150 including an opening 118. The slideable member 150 is slideably mounted in a slot 120 located in the anterior face 30 of the body portion 2. Note that the posterior face of may also include such a slot, for a more secure mounting of the slideable member 150. The opening 118 is sized and shaped snugly to receive an end of the first arm 32 of the resection guide 34. It is again envisaged that the connection arrangement between the first arm 32 and the openings 118 could be reversed for instance the slideable member 150 may include a peg for receipt in an opening located on the end of the first arm 32 of the resection guide 34. As with the row of openings 18 described above in relation to the embodiment of FIG. 4, the slot 120 may be oriented in a direction substantially perpendicular to the resection plane indicated by the resection guide 34.

The slideable member 150 can be slid back and forth within the slot 120 to place the resection plane indicator at a position according to the measured radius/diameter of the femoral head 62. This may allow for finer (i.e. continuous) adjustment of the position of the resection plane indicator than the provision of discrete openings 18 of the kind described above in relation to FIGS. 1 to 4. The slot may be provided with markings 124 such as a scale, which can be referred to by the surgeon, for placing the slideable member in the correct position according to the measured radius/diameter of the femoral head 62.

In the embodiments described above, the resection guide 34 is removably mountable on the body portion 2. However, in the case of the embodiment of FIG. 5, it is envisaged that the resection guide 34 may be integrally formed with the slideable member 150, whereby the resection guide 34 is permanently attached to the body portion 2.

Accordingly, there has been described a surgical device and method for performing a controlled resection of the neck of a femur during a hip replacement procedure. The surgical device includes a body portion having a mounting portion. The mounting portion is mountable on a femoral head of the femur to position the body portion with respect to a center of the femoral head. The surgical device also includes a resection guide. The resection guide is adjustably locatable at a plurality of positions on the body portion for positioning a resection plane indicator of the resection guide with respect to the neck of the femur according to a measured radius/diameter of the femoral head. The method includes measuring the radius/diameter of the femoral head. The method also includes mounting the mounting portion on the femoral head. The method further includes locating the resection guide on the body portion for positioning the resection plane indicator with respect to the femur according to the measured radius/diameter of the femoral head. The method also includes using the resection plane indicator to either mark the position of the resection plane on the neck of the femur or guide a blade of a cutting device to resect the neck of the femur.

Although particular embodiments of the invention have been described, it will be appreciated that many modifications/additions and/or substitutions may be made within the scope of the claimed invention.

The invention claimed is:

1. A surgical device for performing a controlled resection of the neck of a femur during a hip replacement procedure, the surgical device comprising:

a body portion comprising:
   a mounting portion slidably coupled to the body portion, said mounting portion mountable on an anterior aspect of a femoral head of the femur to position the body portion with respect to a center of the femoral head;
   a second mounting portion, wherein the second mounting portion is mountable on a superior aspect or on a superior lateral aspect of the femoral head while the anteriorly mountable mounting portion is mounted on the anterior aspect of the femoral head; and
   a slidable member defining an opening extending therethrough for mounting the body portion on an intramedullary pin extending along a longitudinal axis located in an intramedullary canal of the femur; and
a resection guide, wherein the resection guide is adjustably locatable at a plurality of positions on the body portion for positioning a resection plane indicator of the resection guide with respect to the neck of the femur according to a measured radius/diameter of the femoral head;
wherein the body portion includes a plurality of discrete connection features, each discrete connection feature for mounting the resection guide on the body portion to place the resection plane indicator at a respective position according to the measured radius/diameter of the femoral head;
wherein the anteriorly mountable mounting portion is configured for slidable adjustment along first markings of the body portion in a direction parallel to the longitudinal axis of the intramedullary pin to measure the radius/diameter of the femoral head, and the slidable member is configured for adjustable sliding along second markings the body portion in a direction perpendicular to the longitudinal axis of the intramedullary pin for measuring a femoral offset of the femur.

2. The surgical device of claim 1, wherein each of the connection feature comprises an opening in the body portion within which a mounting member of the resection guide is receivable.

3. The surgical device of claim 1, wherein the resection guide is removably mountable on the body portion.

4. The surgical device of claim 1, wherein the resection plane indicator comprises a guide slot or a guide surface.

5. The surgical device of claim 4, wherein the guide slot or guide surface is a cutting slot or a cutting guide surface for receiving a blade of a cutting device during said resection of the neck.

6. The surgical device of claim 1, wherein the or each mounting portion comprises a substantially circular femoral head contacting surface.

* * * * *